United States Patent
Green et al.

(10) Patent No.: US 6,361,487 B1
(45) Date of Patent: Mar. 26, 2002

(54) METHOD AND APPARATUS FOR BRACHYTHERAPY TREATMENT OF PROSTATE DISEASE

(75) Inventors: Thomas C. Green, Seattle, WA (US); Michael J. Horzewski, San Jose, CA (US)

(73) Assignee: Neoseed Technology LLC, San Francisco, CA (US)

( * ) Notice: Subject to any disclaimer, the term of this patent is extended or adjusted under 35 U.S.C. 154(b) by 0 days.

(21) Appl. No.: 09/522,282

(22) Filed: Mar. 9, 2000

(51) Int. Cl.[7] .............................................. A61M 36/00
(52) U.S. Cl. ................................................. 600/7; 600/6
(58) Field of Search ................................ 600/1, 2, 3, 4, 600/5, 6, 7, 8, 9–595

(56) References Cited

U.S. PATENT DOCUMENTS

| | | | |
|---|---|---|---|
| 4,086,914 A | 5/1978 | Moore | 128/1.2 |
| 4,167,179 A | 9/1979 | Kirsch | 128/1.2 |
| 4,402,308 A | * 9/1983 | Scott | 600/7 |
| 4,700,692 A | 10/1987 | Baumgartner | 128/1.2 |
| 4,815,449 A | 3/1989 | Horowitz | 600/7 |
| 5,460,592 A | 10/1995 | Langton et al. | 600/7 |
| 5,626,829 A | 5/1997 | Koutrouvelis | 424/1.11 |
| 5,871,448 A | 2/1999 | Ellard | 600/459 |
| 5,928,130 A | 7/1999 | Schmidt | 600/7 |
| 5,938,583 A | 8/1999 | Grimm | 600/7 |
| 5,957,935 A | 9/1999 | Brown et al. | 606/130 |
| 5,997,462 A | 12/1999 | Loffler | 600/3 |

FOREIGN PATENT DOCUMENTS

WO  WO 99/20337  4/1999  .......... A61M/36/00

OTHER PUBLICATIONS

Peter Grimm, "Ultrasound Guided Implantation of the Prostate: A Practical Review Course," *Northwest Prostate Institute, Swedish Medical Center*, Seattle, Washington May, 1999.

* cited by examiner

*Primary Examiner*—Robert L. Nasser
*Assistant Examiner*—Pamela Wingood
(74) *Attorney, Agent, or Firm*—Fish & Neave; Nicola A. Pisano

(57) ABSTRACT

Methods and apparatus are provided for brachytherapy treatment of prostate disease. The apparatus comprises a housing, a plunger, a needle, and a lock. The plunger is rigidly affixed to the housing. The lock selectively restricts motion of the needle relative to the plunger. The needle comprises a screw thread that engages the housing or plunger. Rotation of the needle with respect to the housing/plunger causes distal advancement or proximal retraction of the needle with respect to the plunger, providing improved control over delivery of radioactive seeds to a diseased portion of a prostate.

31 Claims, 9 Drawing Sheets

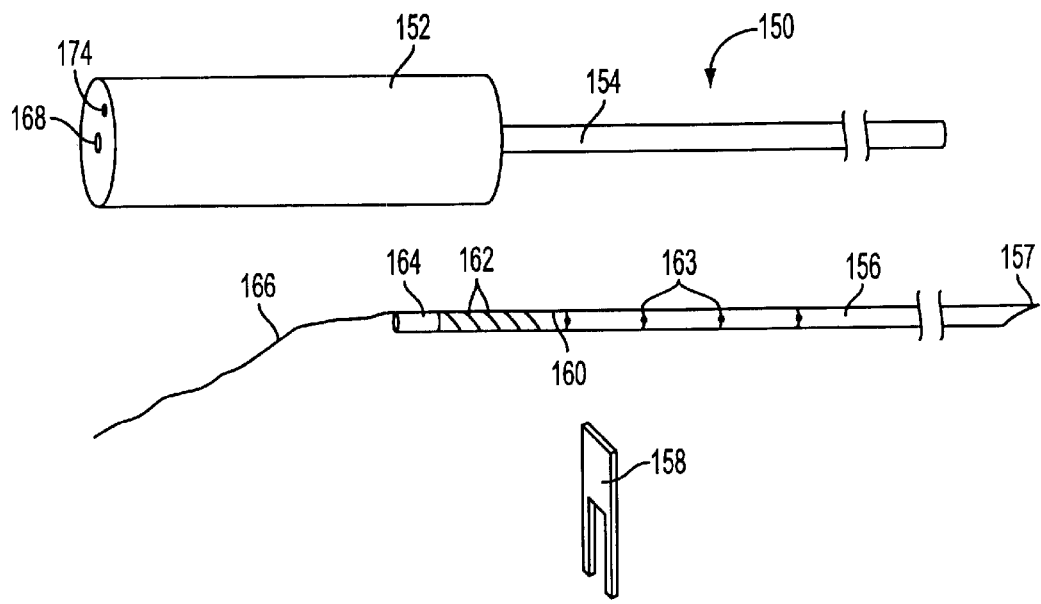
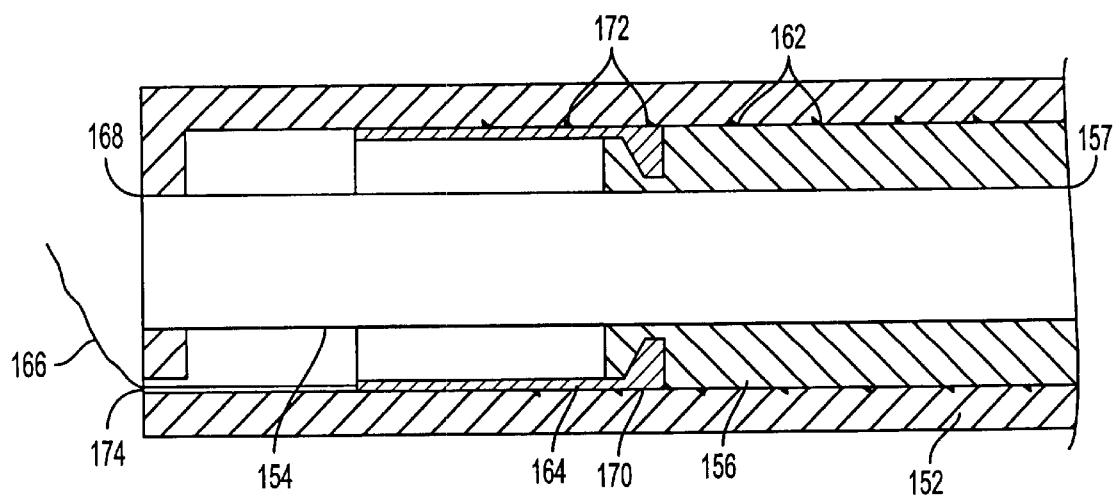
FIG. 7

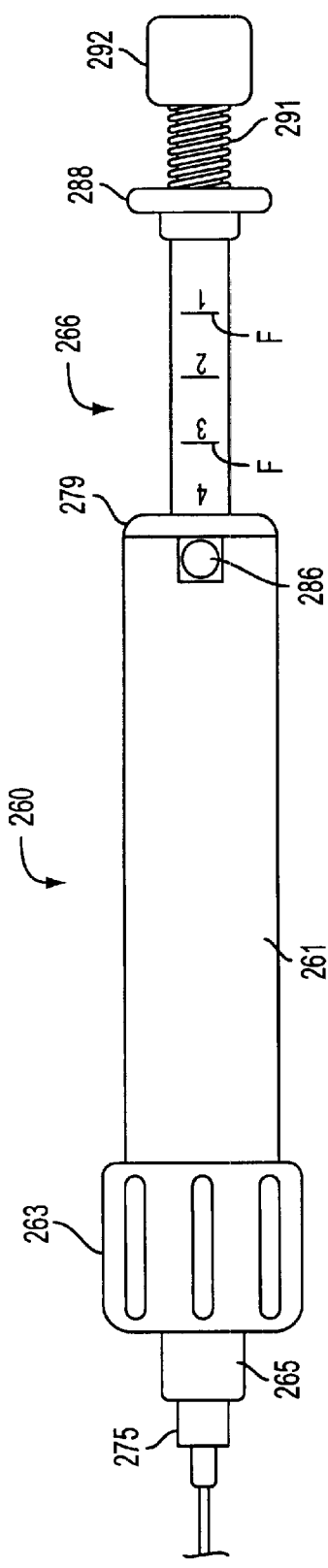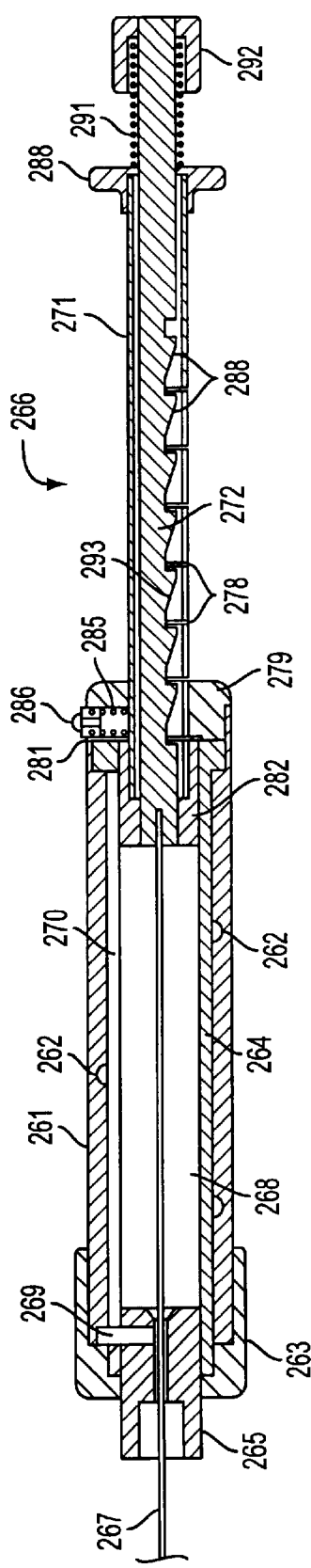
FIG. 13
FIG. 14A

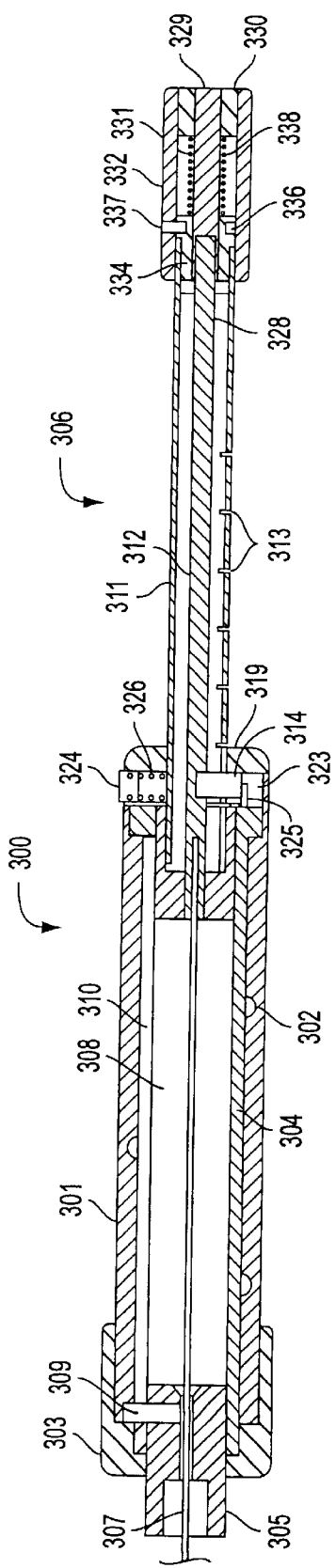
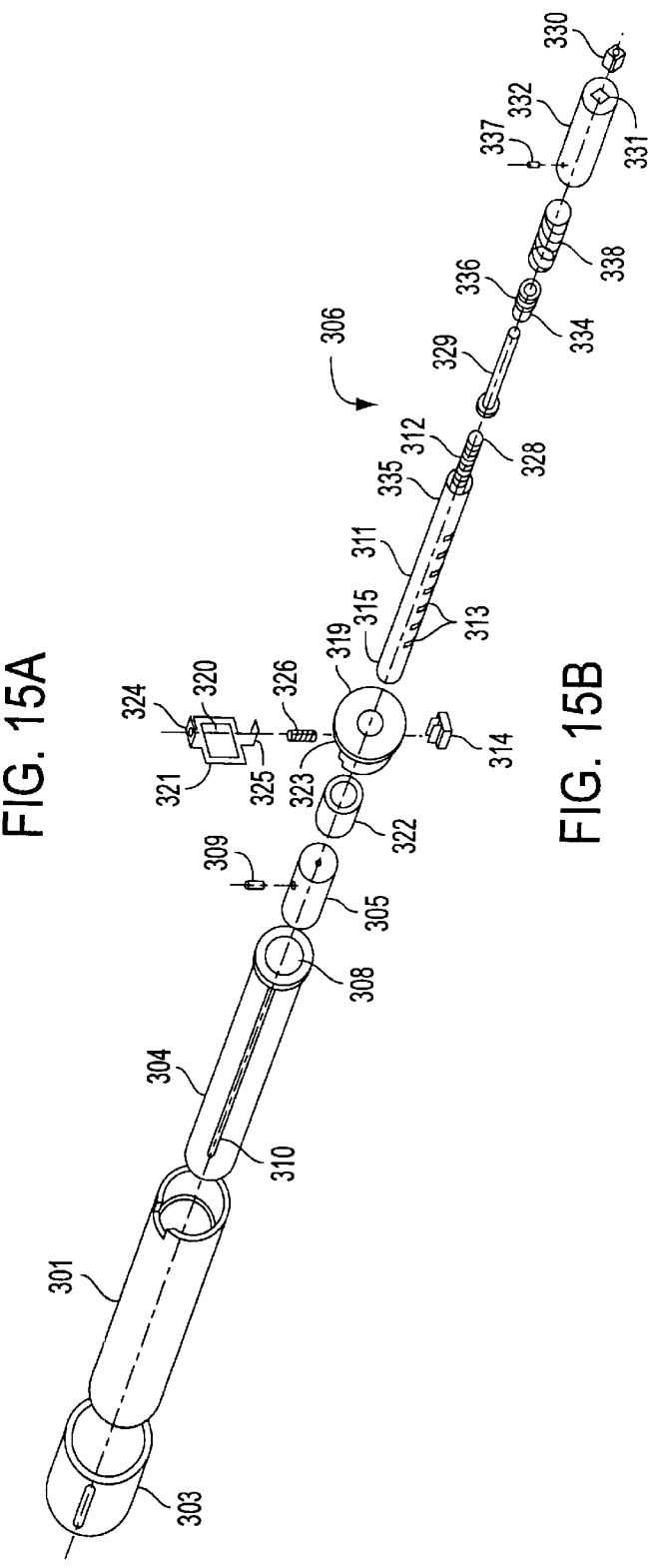
FIG. 15A
FIG. 15B

METHOD AND APPARATUS FOR BRACHYTHERAPY TREATMENT OF PROSTATE DISEASE

FIELD OF THE INVENTION

This invention relates to improved apparatus and methods for the treatment of prostate cancer. More particularly, the present invention provides improved methods and apparatus for administering brachytherapy.

BACKGROUND OF THE INVENTION

Excluding nonmelanoma skin cancers, prostate cancer is the most common cancer afflicting American men. The American Cancer Society estimates that over 180,00 new cases will be diagnosed in the U.S. in the year 2000 alone, and that nearly 32,000 people will die from the disease. Prostate cancer is second only to lung cancer as the leading cause of cancer death in men, accounting for roughly 11%.

Prostate cancer is defined as malignant tumor growth within the prostate gland. Its cause is unknown, although high dietary fat intake and increased testosterone levels are believed to be contributory factors. A letter scale ("A" through "D"), which accounts for the location of the cancer, is commonly used to classify the stage of disease. In Stage A, the tumor is not palpable but is detectable in microscopic biopsy. Stage B is characterized by a palpable tumor confined to the prostate. By Stage C, the tumor extends locally beyond the prostate with no distant metastasis. By Stage D, cancer has spread to the regional lymph nodes or has produced distant metastasis.

In the early stages, prostate cancer is most commonly treated by prostate removal or by brachytherapy. More advanced cases are treated by hormonal manipulation or orchiectomy to reduce testosterone levels and curb spreading of the disease, by chemotherapy, or by external beam radiation therapy.

With regard to treatment of early stage prostate cancer, the state of the art has several drawbacks. Radical prostatectomy is often recommended for treatment of localized stage A and B prostate cancers. Under general or spinal anesthesia, an incision is made through a patient's abdomen or perineal area, and the diseased prostate is removed. The procedure is lengthy, especially if a lymph node dissection is simultaneously performed, and requires a hospital stay of 2–5 days. Possible complications include impotence and urinary incontinence.

Internal radiation therapy or brachytherapy has recently been modified and holds great promise for the treatment of early stage prostate cancer. Radioactive pellets or seeds of, for example, iodine-125, gold-198, palladium-103, ytterbium-169, or iridium-192, are deposited directly into the prostate through needle placement. Imaging tests, such as transrectal ultrasound, CT scans, or MRI, are used to accurately guide placement of the radioactive material. Advantageously, radiation is administered directly to the prostate with less damage to surrounding tissues, requiring a significantly smaller radiation dosage as compared to external beam radiation therapy. Furthermore, the procedure need only be performed once. Complications include a lower, yet still significant, incidence of impotence and urinary incontinence, compared to prostate removal procedures.

The radioactive seeds are placed inside thin needles, which are inserted through the skin of the perineum (area between the scrotum and anus) into the prostate. U.S. Pat. No. 5,928,130 to Schmidt provides a slightly modified example of such a needle device. Each needle is slowly retracted with a spinning motion by a first practitioner while a plunger within the needle, and proximal of the radioactive seeds, is held stationary by a second practitioner. The plunger keeps the seeds in place during retraction of the needle, while rotation of the needle during retraction prevents jamming of the seeds while delivering the seeds in a line within the prostate.

The seeds, which are permanently implanted, give off radiation for weeks or months. Their presence causes little discomfort, and they are left in the prostate after decay of the radioactivity. For about a week following needle insertion, patients may experience pain in the perineal area, and urine may have a red-brown discoloration.

Although, when performed correctly, radioactive seed implantation may provide several benefits, compared to prostate removal and other techniques, current surgical apparatus and methods for delivering the seeds to target locations within the prostate are somewhat crude and are subject to practitioner error. The procedure requires two practitioners working cooperatively to deliver the seeds. The depth to which the plunger is inserted into the needle, in the loaded and advanced states, is critical but crudely measured. The plunger and needle may accidentally move relative to one another during needle insertion or seed delivery, causing improper positioning of deposited seeds. The needle is somewhat flexible and should be inserted quickly to minimize bending at its distal tip, but this is often not done due to inexperience or technical ability of the practitioners, or to avoid potential relative movement between the plunger and the needle.

Attempts have been made to address various aspects of these concerns. For example, U.S. Pat. No. 4,815,449 to Horowitz describes an absorbable member with seeds spaced within the member to facilitate proper spacing during delivery. U.S. Pat. No. 4,700,692 to Baumgartner describes apparatus for delivering all of the seeds simultaneously. PCT document WO 99/20337 to Rydell describes a gun-like apparatus for delivering seeds once the needle has been inserted into the prostate.

While each of these devices may provide some benefit over the prior art, none satisfactorily addresses the shortcomings of current techniques. In view of the drawbacks associated with previously-known methods and apparatus for brachytherapy, it would be desirable to provide methods and apparatus that overcome such drawbacks.

It further would be desirable to provide methods and apparatus that allow efficient preparation of the apparatus for therapeutic administration.

It still further would be desirable to provide methods and apparatus for administering brachytherapy that require only one medical practitioner.

It further would be desirable to provide methods and apparatus that yield easy measurement and maintenance of plunger depth within the needle.

It would also be desirable to provide methods and apparatus for brachytherapy that allow rapid insertion of the needle while maintaining the distance between the needle and plunger.

SUMMARY OF THE INVENTION

In view of the foregoing, it is an object of the present invention to provide methods and apparatus for brachytherapy that overcome drawbacks associated with previously-known methods and apparatus.

It is also an object of the present invention to provide methods and apparatus that allow efficient preparation of the apparatus for therapeutic administration.

It is another object to provide methods and apparatus for brachytherapy that require only one medical practitioner.

It is yet another object to provide methods and apparatus that yield easy measurement and maintenance of plunger depth within the needle.

It still further is an object of the present invention to provide methods and apparatus for brachytherapy that allow rapid insertion of the needle while maintaining the distance between the needle and plunger.

These and other objects of the present invention are accomplished by providing methods and apparatus for brachytherapy treatment of prostate cancer comprising a specialized housing that maintains needle/plunger spacing, provides easy measurement of plunger depth within the needle, requires only one practitioner to operate, and enables rapid needle insertion. The plunger is fixed with respect to the housing, while the needle is removably coupled to the housing. Either the plunger or the housing wall is threaded to receive the needle. Measurement indicia on the needle simplify determination of plunger depth within the needle. A locking mechanism maintains plunger depth during needle insertion. To deliver seeds, the needle is rotated while the housing is held stationary, causing the needle to retract along the screw thread.

In a preferred embodiment, the needle is rotated manually. Alternatively, the needle may attach to a swivel that rotates the needle by pulling it proximally along the screw thread. In a still further embodiment, a pull tab may be used to rotate the needle.

Methods of using the present invention are also provided.

BRIEF DESCRIPTION OF THE DRAWINGS

Additional objects and advantages of the invention will be apparent from the following description, the accompanying drawings and the appended claims, in which:

FIG. 6 is an isometric exploded view of a further alternative embodiment of the present invention comprising a swivel;

FIG. 7 is a cross-sectional view of the apparatus of FIG. 6;

DETAILED DESCRIPTION OF THE INVENTION

The present invention provides methods and apparatus for improved administration of brachytherapy. More particularly, the present invention provides a threaded housing with locking mechanism that maintains the position of the plunger with respect to the needle and provides controlled retraction of the needle.

Figure 1:
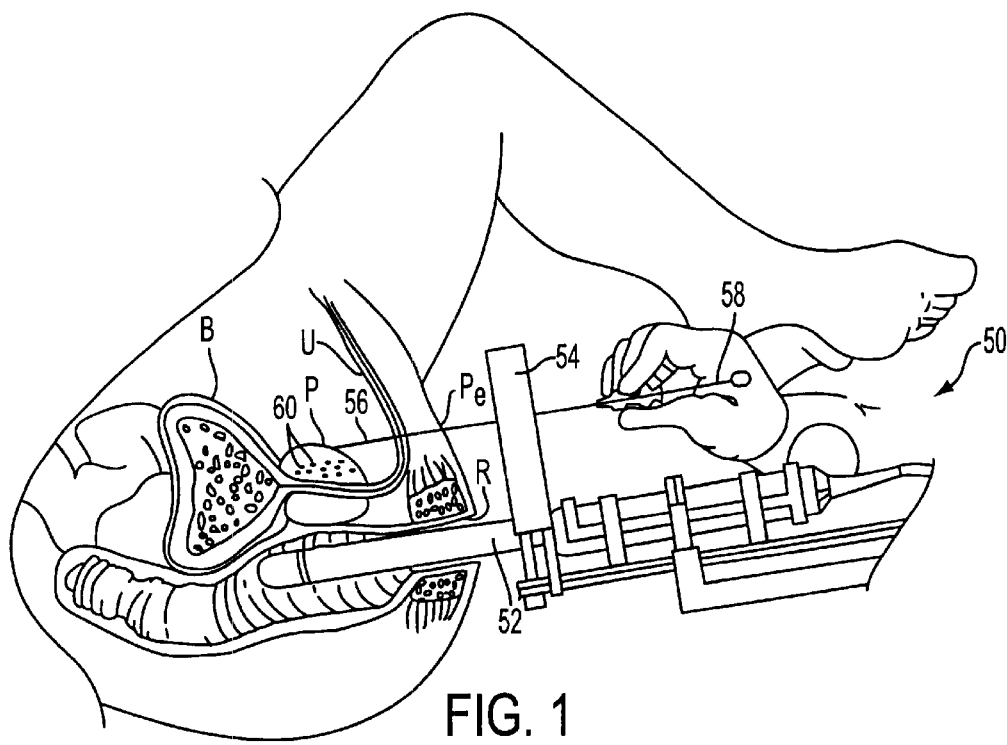
FIG. 1 is a schematic view of a prior art method of performing brachytherapy.

Referring now to FIGS. 1 and 2A–2G, the prior art method of performing brachytherapy is described. The method and apparatus are as taught by Peter Grimm, DO, in a pamphlet entitled, "Ultrasound Guided Implantation of the Prostate: A Practical Review Course." As seen in FIG. 1, brachytherapy apparatus 50 comprises transrectal ultrasound probe 52, guide block 54, needle 56, plunger 58, and radioactive seeds 60. Ultrasound probe 52 is advanced through a patient's rectum R to facilitate imaging of the patient's prostate P. Prostate P surrounds the urethra U and is just proximal of the bladder B. Needle 56, loaded with seeds 60 and plunger 58, is advanced through the patient's perineum Pe into prostate P, where needle 56 is retracted and seeds 60 are delivered to the patient.

With reference to FIGS. 2, a previously known seed delivery method is described in greater detail. Needle 56 has proximal end 62, sharpened distal end 64, and a lumen extending therebetween. Proximal end 62 comprises hub 66 for easy grasping of the needle. The opening at the distal tip of needle 56 is initially filled with bone wax that melts when placed inside the body. The needle lumen typically is filled in an alternating pattern of seeds 60 and spacers 68.

Figure 2A:
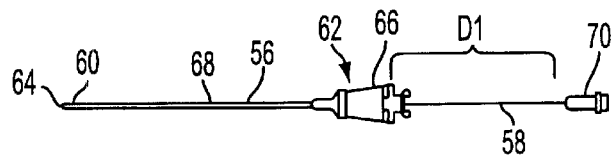
FIGS. 2A–2G are schematic views detailing the prior art method in greater detail.

Once a required number of seeds have been loaded, plunger 58 is inserted into proximal end 62 of needle 56 and is advanced distally until it abuts the proximal-most seed. Plunger 58 comprises grip 70 at its proximal end. The distance from the distal end of grip 70 to the distal end of the plunger is equal to the length of needle 56. Thus, since seeds 60 and spacers 68 are of known length, measurement of D1, the distance plunger 58 extends proximally of needle 56 in the loaded configuration, provides verification of the number of seeds 60 located within the needle lumen, as seen in FIG. 2A.

Figure 2B:
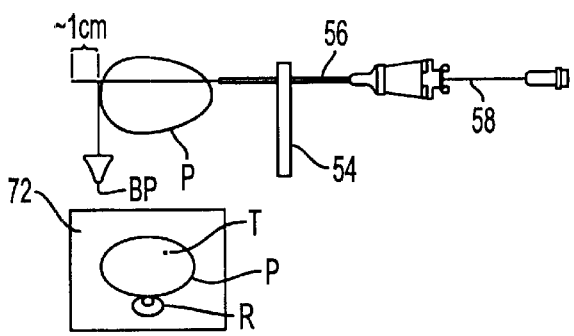
Figure 2C:
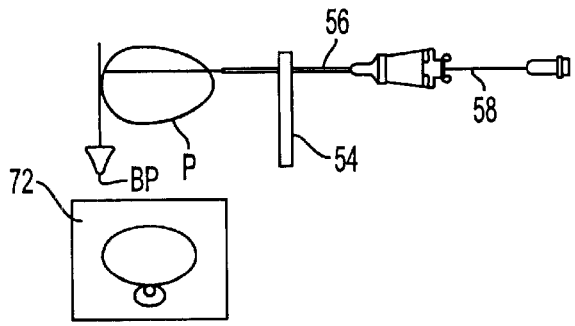
Figure 2D:
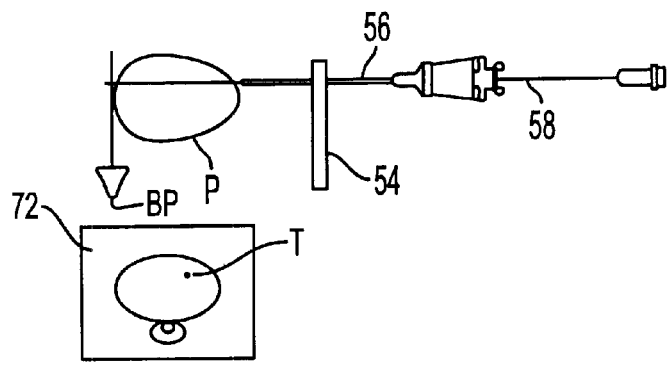

Ultrasound probe 52 provides signals that are converted by a previously known ultrasound system to display ultrasonic image 72 of base plane BP, which is located tangent to the distal surface of prostate P. All positions within the prostate are determined relative to base plane BP. With seeds 60 loaded into needle 56 and the distance D1 verified; the needle, seeds, and plunger 58 are inserted through guide block 54 and into the patient until needle 56 appears as target T on ultrasonic image 72 and extends about a centimeter distal of base plane BP, as depicted in FIG. 2B. The apparatus is then retracted until target T disappears (FIG. 2C) and is once again advanced until target T just reappears (FIG. 2D). All the while, distance D1 is maintained.

Figure 2E:
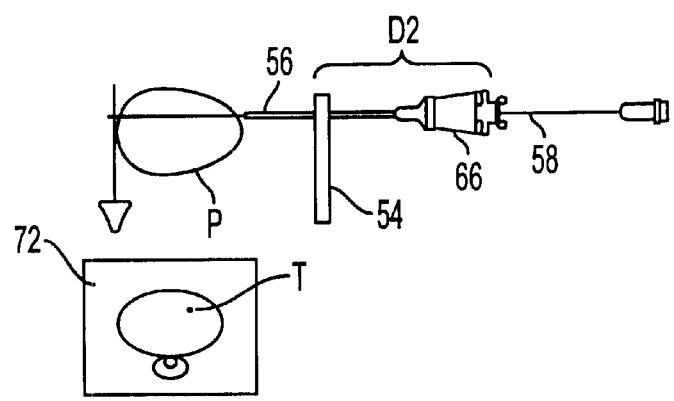
Figure 2F:
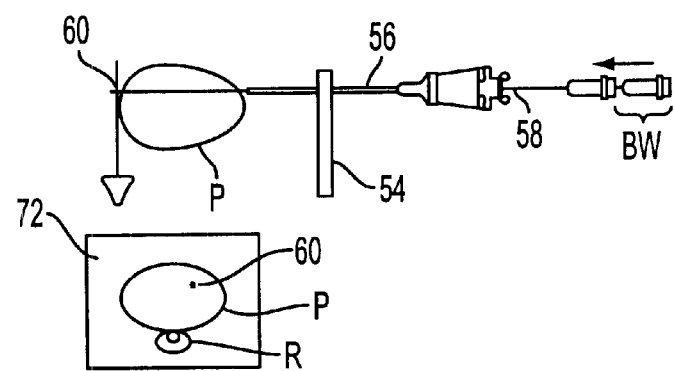

Once needle 56 is aligned with base plane BP, a distance D2 between the proximal face of guide block 54 and the proximal face of hub 66 is established, as shown in FIG. 2E. D2 serves as the reference distance for determining insertion depth for all subsequent needle insertions. A first medical practitioner then holds needle 56 stationary while a second medical practitioner advances the first seed 60 to the distal tip of the needle with plunger 58, as depicted in FIG. 2F. The advancement distance equals the length BW of the bone wax used to plug the tip.

Figure 2G:
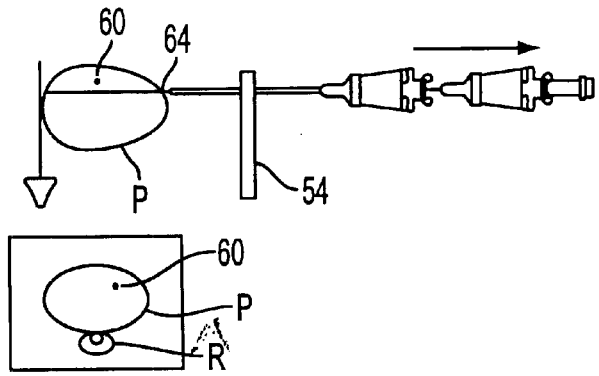

Finally, the second medical practitioner holds plunger 58 stationary while the first practitioner rotates and proximally retracts needle 56 to sew the seeds in a line within prostate P, as shown in FIG. 2G. The needle and plunger are then removed from the patient, and the procedure is repeated at other locations as necessary.

Figure 3:
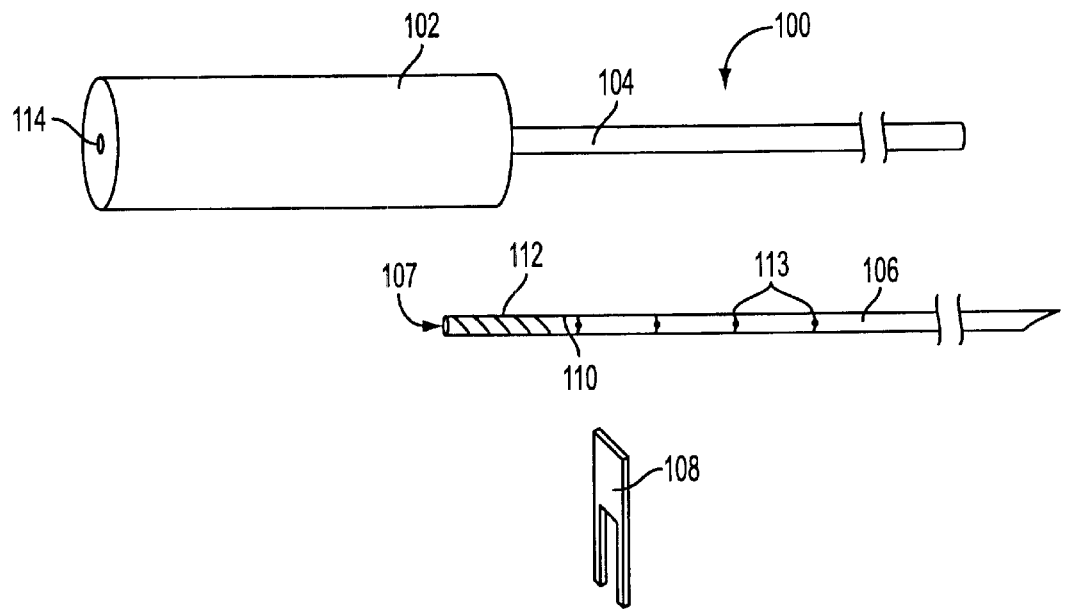
FIG. 3 is an isometric exploded view of a first embodiment of apparatus constructed in accordance with the present invention.
Figure 4:
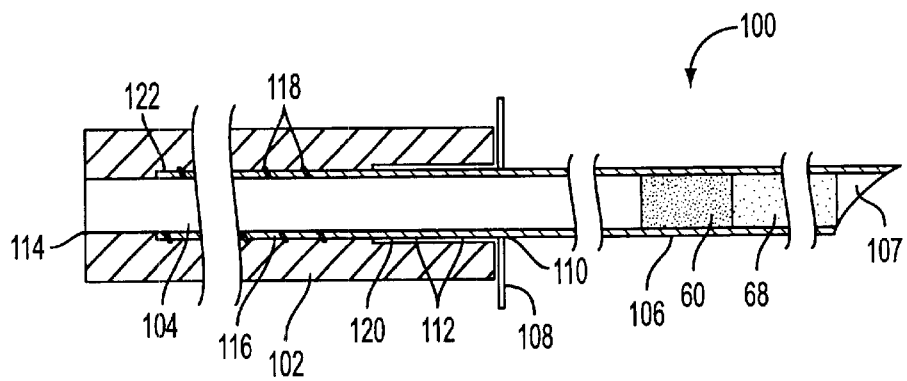
FIG. 4 is a cross-sectional view of the apparatus of FIG. 3.

With reference now to FIGS. 3 and 4, a first embodiment of apparatus constructed in accordance with he present invention is described. Apparatus 100 comprises housing 102, plunger 104, needle 106, and lock 108. Lock 108 is configured to be received in slot 110 of needle 106. Needle 106 further comprises lumen 107, male screw thread 112, and measurement indicia 113. Housing 102 comprises lumen 114, in which plunger 104 is rigidly fixed, threaded bore 116 with female screw thread 118, and standard bore 120. When assembled, male thread 112 of needle 106 engages female thread 118 of housing 102, and plunger 104 extends into lumen 107 of needle 106.

A method of using apparatus 100 in accordance with the principles of the present invention is now described. Needle 106, loaded with seeds 60 and spacers 68 in lumen 107, is inserted through bore 120 until male thread 112 of needle 106 just mates with female thread 118 of bore 116.

At this point, plunger 104 extends partially within lumen 107 of needle 106, so that plunger 104 just contacts the proximal-most seed 60. Also, slot 110 of needle 106 is just distal of the opening to bore 120. Lock 108 is removably received within slot 110 and ensures that plunger 104 is not advanced distally with respect to needle 106 until the needle is inserted within a patient's prostate. Lock 108 thereby ensures that distance D1 between the proximal end of needle 106 and proximal base 122 of bore 116 (which is roughly equal to the length of bore 116) is maintained during insertion. Since D1 is positively maintained during insertion, the apparatus of the present invention should advantageously cause medical practitioners to be less reticent about rapid insertion of the needle into a patient.

Measurement indicia 113 of needle 106 permit easy determination of distance D1, and, thus, verification of the number of seeds 60 contained within lumen 107 of needle 106. As an illustrative example, D1 is such that the proximal-most indicator mark 113 extends beyond the distal end of housing 102. If this marking is '0', the proximal end of needle 106 is in contact with proximal base 122 of bore 116. If it is '1', there is one centimeter of separation, etc.

After insertion of the needle into the patient, lock 108 is removed, thereby allowing relative movement between plunger 104 and needle 106. Initially, needle 106 is held stationary while housing 102 is rotated to advance the distal-most seed 60 to the tip of needle 106. Then, housing 102 is held stationary while needle 106 is rotated. This causes needle 106 to retract proximally along thread 118 while plunger 104 remains stationary, thereby controllably sewing seeds 60 in a row in the prostate. Since the sewing motion is simplified, compared to prior art apparatus 50, only one practitioner is required to perform the procedure.

The distance D1 may be altered as needed by altering the length of bore 116 and, thus, the length of housing 102. Alternatively, bore 116 may be of a standard length in excess of that required for D1. Needle 106 then may comprise multiple slots 110 along its length to receive lock 108. The distance D1 then may be fixed at a variety of lengths.

Figure 5:
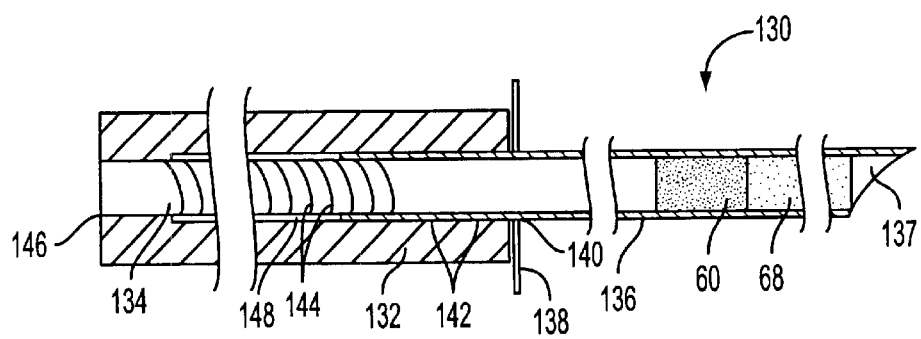
FIG. 5 is a cross-sectional view of an alternative embodiment of apparatus of the present invention.

Referring now to FIG. 5, an alternative embodiment of the present invention is disclosed. Apparatus 130 comprises housing 132, plunger 134, needle 136, and lock 138. Lock 138 is configured to be received in slot 140 of needle 136. Needle 136 further comprises lumen 137, female screw thread 142 along the walls of the proximal portion of its lumen, and measurement indicia (not shown). Plunger 134 comprises male screw thread 144 along its proximal end. Housing 132 comprises lumen 146, in which plunger 134 is rigidly fixed, and bore 148.

Needle 136, loaded with seeds 60 and spacers 68, is inserted through bore 148 until female thread 142 of needle 136 just mates with male thread 144 of plunger 134. Thus, apparatus 130 is similar to apparatus 100, except that needle 136 threadingly engages plunger 134, rather than the housing.

With reference to FIGS. 6 and 7, a further alternative embodiment of the present invention is detailed. Apparatus 150 comprises housing 152, plunger 154, needle 156, and lock 158. Lock 158 is configured to be received in slot 160 of needle 156. Needle 156 further comprises lumen 157, male screw thread 162, measurement indicia 163, and swivel 164 including cord 166. Housing 152 comprises lumen 168, in which plunger 134 is rigidly fixed; threaded bore 170 with female screw thread 172; and a standard bore (not shown) similar to bore 120 of apparatus 100. Housing 152 further comprises cord bore 174 through which cord 166 passes out of housing 152.

In use, cord 166 is threaded through cord bore 174 and the male and female screw threads are engaged as described hereinabove with reference to apparatus 100. Needle 156 then may be retracted proximally with respect to housing 152 by holding the housing stationary and pulling cord 166 proximally. The needle rotates and retracts within the screw thread, while swivel 164 moves proximally in bore 168, but does not rotate.

Figure 8:
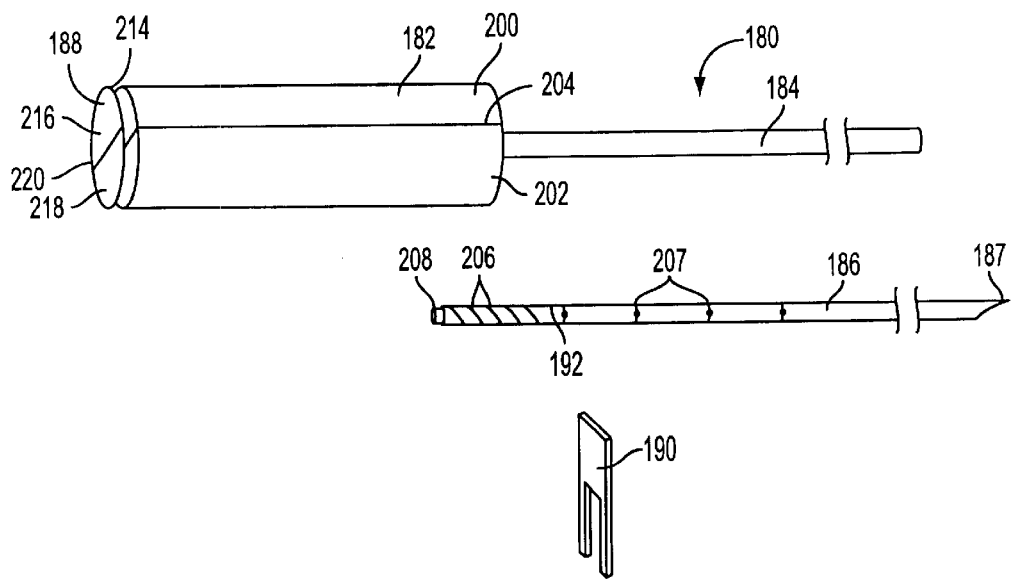
FIG. 8 is an isometric exploded view of a still further alternative embodiment with a syringe swivel.
Figure 9:
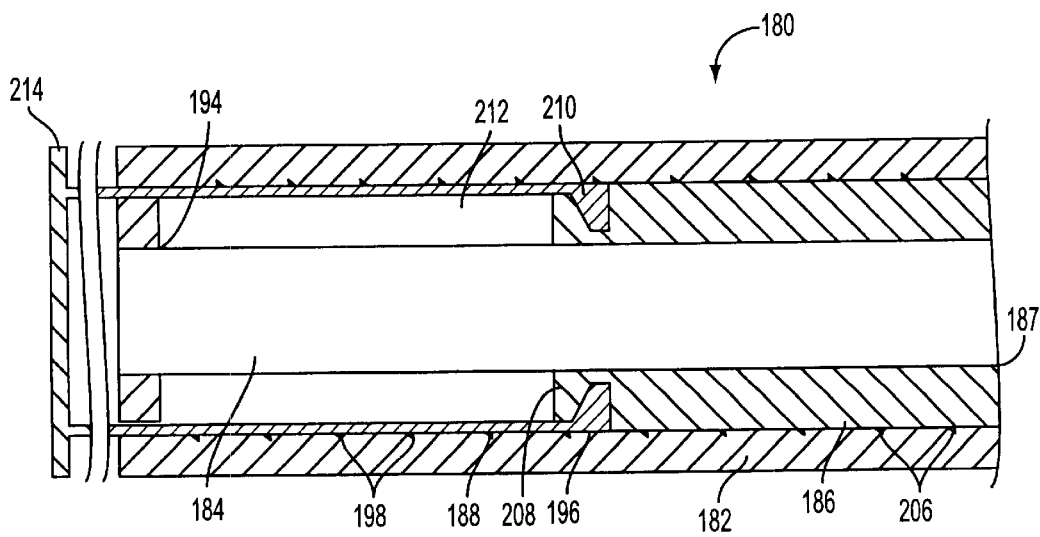
FIG. 9 is a cross-sectional view of the apparatus of FIG. 8.

Referring now to FIGS. 8 and 9, a still further alternative embodiment of the present invention is described. Apparatus 180 comprises housing 182, plunger 184, needle 186, syringe swivel 188, and lock 190. Lock 190 is configured to be removably received in slot 192 of needle 186. Housing 182 comprises lumen 194, in which plunger 184 is rigidly fixed; threaded bore 196 with female screw thread 198; and a standard bore (not shown) similar to bore 120 of apparatus 100. Housing 182 is formed in two halves 200 and 202 joined at hinge 204. Hinge 204 preferably is a 'living hinge' as may be constructed using polymers, such as polypropylene, and previously known manufacturing techniques. Needle 186 further comprises lumen 187, male screw thread 206, measurement indicia 207, and swivel attachment 208. Syringe swivel 188 comprises swivel attachment 210, bore 212, and enlarged proximal end 214, and is formed in two halves 216 and 218 joined at hinge 220. As with hinge 204, hinge 220 preferably comprises a living hinge.

Housing 182 and syringe swivel 188 are opened at hinges 204 and 220, respectively, so that swivel 20 attachments 208 and 210, and the male and female screw threads, engage each other. The housing and syringe swivel are then closed. After insertion into a patient, needle 186 may be retracted proximally with respect to housing 182 by holding the housing stationary and retracting enlarged end 214 of syringe swivel 188 proximally. Needle 186 rotates and retracts within the screw thread while syringe swivel 188 moves proximally but does not rotate.

Figure 10:
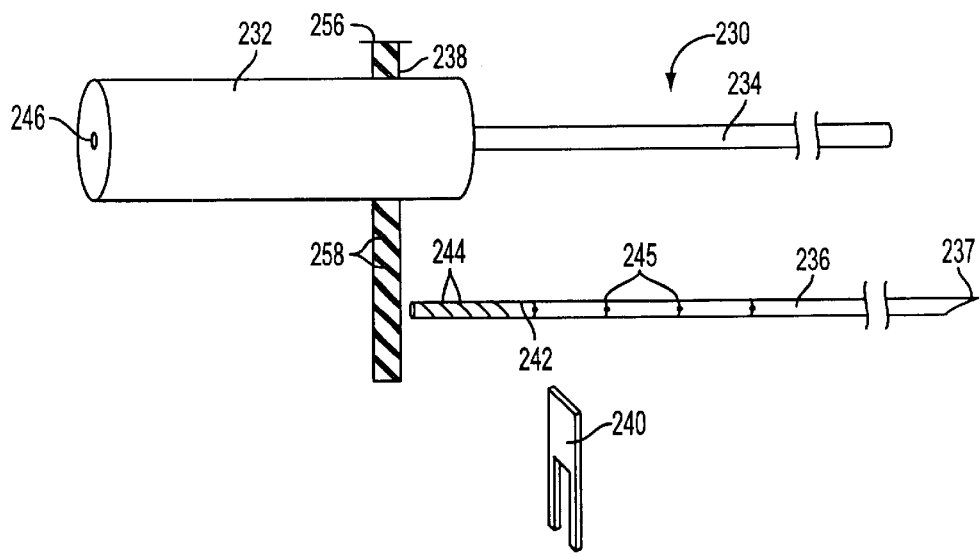
FIG. 10 is an isometric exploded view of yet another alternative embodiment of apparatus constructed in accordance with the present invention comprising a pull tab.
Figure 11:
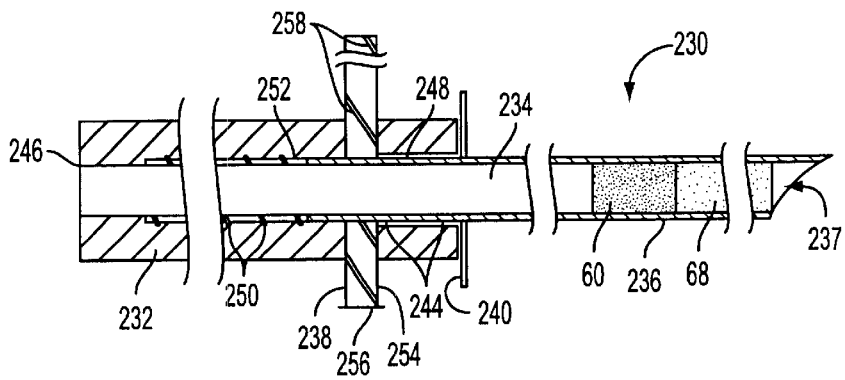
FIG. 11 is a cross-sectional view of the apparatus of FIG. 10.
Figure 12:
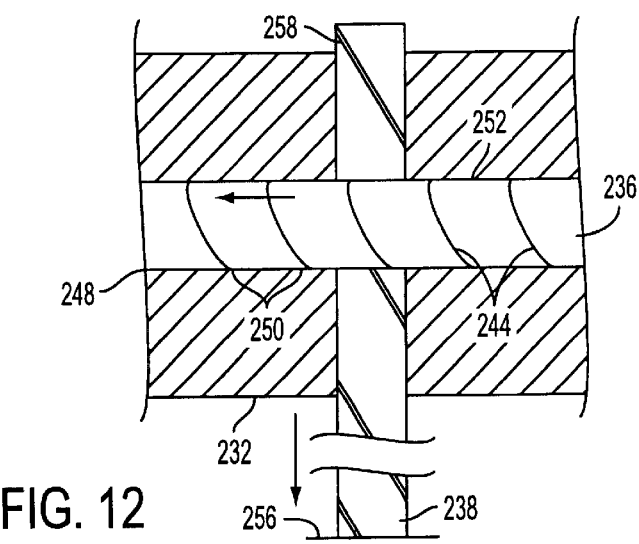
FIG. 12 is a detail view of the cross-section of FIG. 11.
Figure 14B:
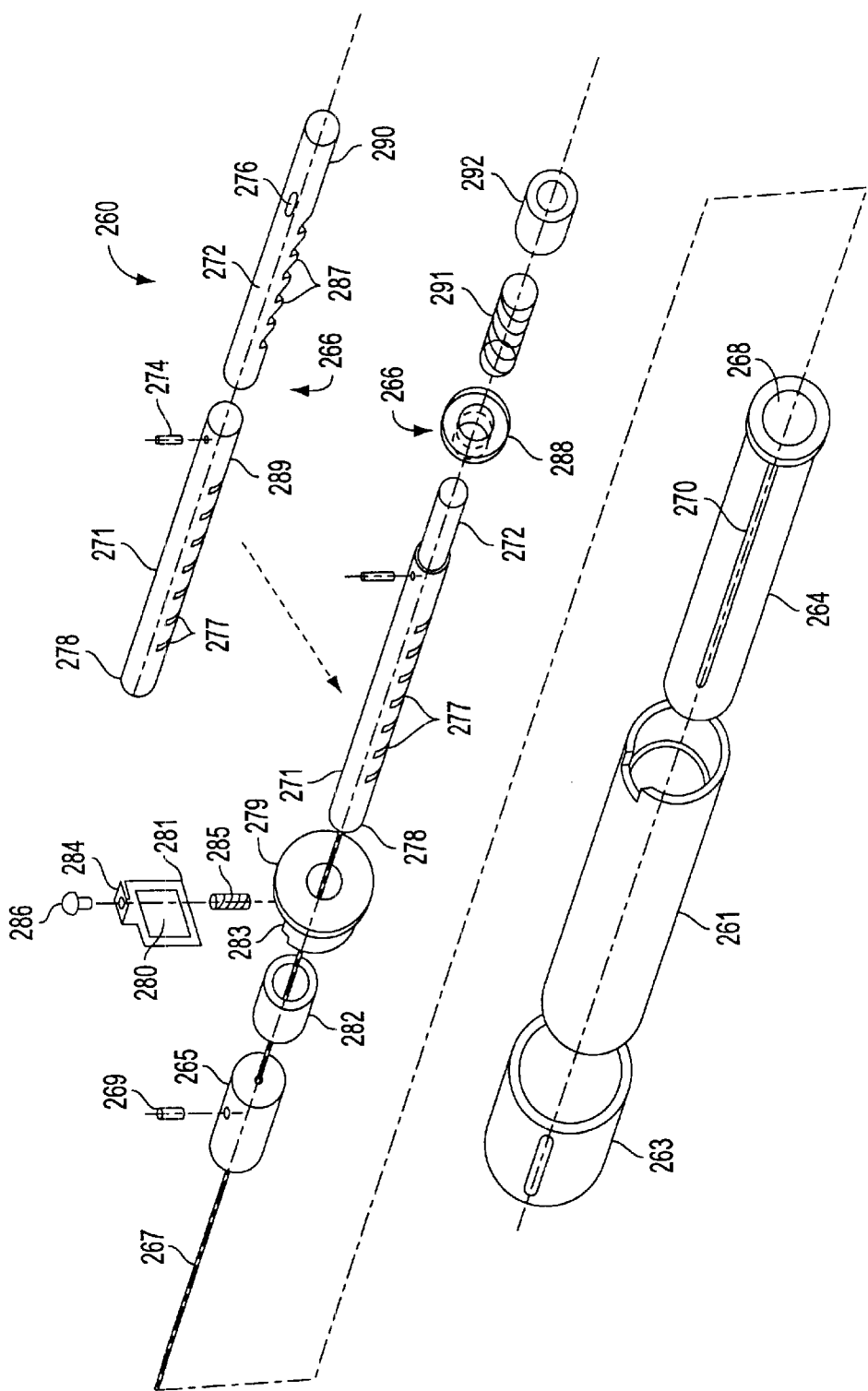

With reference to FIGS. 10–12, yet another alternative embodiment of the present invention is described. Apparatus 230 comprises housing 232, plunger 234, needle 236, pull tab 238, and lock 240. Lock 240 is configured to be received in slot 242 of needle 236. Needle 236 further comprises lumen 237, male screw thread 244, and measurement indicia 245. Housing 232 comprises lumen 246, in which plunger 234 is rigidly fixed; threaded bore 248 with female screw thread 250; standard bore 252; and slot lumen 254 configured to receive pull tab 238. Slot lumen 254 is preferably located just off center of the radial axis of housing 232 and communicates with bore 252. Pull tab 238 comprises grip 256 and female threads 258.

Needle 236, loaded with seeds 60 and spacers 68, is inserted through bore 252 into threaded bore 248 until male thread 244 of needle 236 mates with both female screw thread 250 of housing 232 and female threads 258 of pull tab 238. As most clearly illustrated in FIG. 11, needle 236 then may move relative to housing 232 simply by holding housing 232 stationary and pulling or pushing pull tab 238. Pulling tab 238 causes needle 236 to rotate and proximally retract in a controlled fashion along screw thread 250 of housing 232, and along threads 258 of pull tab 238, thereby sewing the seeds along the needle track.

Although particular embodiments of the present invention have been described above in detail, it will be understood that this description is merely for purposes of illustration. Specific features of the invention are shown in some drawings and not in others; this is for convenience only, and any feature may be combined with another in accordance with the invention. Further variations will be apparent to one skilled in the art in light of this disclosure and are intended to fall within the scope of the appended claims.

What is claimed is:

1. Apparatus for performing brachytherapy comprising:
   a housing having a bore and a first screw thread disposed along the bore;
   a plunger affixed to the housing within, and extending out of, the bore; and
   a needle having a proximal end, a sharpened distal end, a mating screw thread on an exterior surface of the needle near the proximal end, and a lumen extending between the proximal and distal ends,
   wherein the plunger extends into the lumen when the mating screw thread engages the first screw thread.

2. The apparatus of claim 1 further comprising a lock configured to selectively restrict relative motion of the plunger with respect to the needle.

3. The apparatus of claim 2 wherein the needle further comprises a slot distal of the first screw thread, and the lock is removably received within the slot.

4. The apparatus of claim 1, wherein the housing further comprises a cord bore extending into the bore, the apparatus further comprising:
   a swivel coupled to the proximal end of the needle; and
   a cord coupled to the swivel and extending through the cord bore.

5. The apparatus of claim 1 further comprising a first swivel attached to the proximal end of the needle.

6. The apparatus of claim 5 further comprising a syringe swivel slidingly received within the bore of the housing, the syringe swivel coupled to the first swivel.

7. The apparatus of claim 6 wherein the housing comprises a first half and a second half, and a first hinge joining the first half to the second half.

8. The apparatus of claim 7 wherein the first hinge comprises a living hinge.

9. The apparatus of claim 7 wherein the syringe swivel comprises a first syringe half and a second syringe half, and a second hinge joining the first syringe half to the second syringe half.

10. The apparatus of claim 9 wherein the second hinge comprises a living hinge.

11. The apparatus of claim 1 wherein the housing further comprises a slot lumen, the slot lumen in communication with the lumen.

12. The apparatus of claim 11 further comprising a pull tab adapted to extend through the slot lumen to engage the needle.

13. The apparatus of claim 12 wherein the pull tab further comprises threads configured to engage the mating screw thread.

14. The apparatus of claim 1 wherein the needle further comprises measurement indicia for determining a depth of the plunger within the lumen.

15. Apparatus for performing brachytherapy comprising:
    a housing having a bore;
    a plunger affixed to the housing within, and extending out of, the bore, the plunger having a first screw thread disposed on an exterior surface of the plunger; and
    a needle having a proximal end, a sharpened distal end, a lumen extending between the proximal and distal ends, and a mating screw thread disposed within the lumen near the proximal end,
    wherein the plunger extends into the lumen when the mating screw thread engages the first screw thread.

16. The apparatus of claim 15 further comprising a lock configured to selectively restrict relative motion of the plunger with respect to the needle.

17. The apparatus of claim 16 wherein the needle further comprises a slot distal of the first screw thread, and the lock is removably received within the slot.

18. The apparatus of claim 15, wherein the housing further comprises a cord bore extending into the bore, the apparatus further comprising:
    a swivel coupled to the proximal end of the needle; and
    a cord coupled to the swivel and extending through the cord bore.

19. The apparatus of claim 15 further comprising a first swivel attached to the proximal end of the needle.

20. The apparatus of claim 19 further comprising a syringe swivel slidingly received within the bore of the housing, the syringe swivel coupled to the first swivel.

21. The apparatus of claim 20 wherein the housing comprises a first half and a second half, and a first hinge joining the first half to the second half.

22. The apparatus of claim 21 wherein the first hinge comprises a living hinge.

23. The apparatus of claim 21 wherein the syringe swivel comprises a first syringe half and a second syringe half, and a second hinge joining the first syringe half to the second syringe half.

24. The apparatus of claim 23 wherein the second hinge comprises a living hinge.

25. The apparatus of claim 15 wherein the needle further comprises measurement indicia for determining a depth of the plunger within the lumen.

26. A method of administering brachytherapy to a target location within a patient, the method comprising:
    providing apparatus comprising a housing assembly with a bore and a plunger fixed within the bore, and a needle with a lumen configured to receive a distal end of the plunger, the needle configured to be received within the bore;
    loading a plurality of radioactive seeds into the needle lumen;
    receiving the distal end of the plunger within the needle lumen until the plunger contacts a distal-most of the plurality of radioactive seeds;

threadingly engaging a proximal end of the needle with the housing assembly;

inserting a sharpened distal tip of the needle into the target location within the patient until it is aligned with a reference plane;

rotating the housing assembly with respect to the needle to advance the plunger distally with respect to the needle and advance a proximal-most of the plurality of radioactive seeds to a distal tip of the needle; and rotating the needle with respect to the housing assembly to retract the needle proximally relative to the plunger, thereby delivering the plurality of radioactive seeds in a row within the patient.

27. The method of claim 26 further comprising sequentially repeating the steps at additional target locations within the patient.

28. The method of claim 26 wherein the needle further comprises a swivel, and wherein proximally retracting the needle relative to the plunger comprises proximally retracting the swivel.

29. The method of claim 28 wherein the swivel comprises a syringe, and wherein proximally retracting the needle further comprises proximally retracting the syringe.

30. The method of claim 26 wherein providing apparatus further comprises providing a pull tab configured to threadingly engage the needle; and wherein proximally retracting the needle relative to the plunger further comprises moving the pull tab to rotate and retract the needle relative to the housing assembly.

31. The method of claim 26 further comprising, prior to inserting the sharpened distal tip of the needle into the target location, verifying that the plurality of radioactive seeds are within the needle lumen.

* * * * *